(12) United States Patent
Urick et al.

(10) Patent No.: US 6,471,671 B1
(45) Date of Patent: Oct. 29, 2002

(54) PRELOADED GAS INFLATION DEVICE FOR BALLOON CATHETER

(75) Inventors: Michael J. Urick, Beaconsfield (CA); Scott Andrus, Santa Fe, NM (US); James G. Hansen, Coon Rapids, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 82 days.

(21) Appl. No.: 09/644,754

(22) Filed: Aug. 23, 2000

(51) Int. Cl.⁷ ................................................ A61M 5/32
(52) U.S. Cl. ..................................... 604/98.01; 604/199
(58) Field of Search ........................... 604/97.01, 97.02, 604/97.03, 98.01, 98.02, 99.01, 181, 182, 187, 199, 200, 212, 218, 244; 606/191, 192

(56) References Cited

U.S. PATENT DOCUMENTS

| | | | |
|---|---|---|---|
| 3,688,765 A | | 9/1972 | Gasaway |
| 3,939,834 A | * | 2/1976 | McMahon ............. 204/192.15 |
| 4,234,026 A | * | 11/1980 | Bayham ..................... 383/210 |
| 4,573,977 A | | 3/1986 | Crawford .................... 604/212 |
| 4,713,060 A | * | 12/1987 | Riuli ........................... 604/199 |
| 4,793,351 A | | 12/1988 | Landman et al. ........... 128/344 |
| 4,795,431 A | | 1/1989 | Walling ........................ 604/97 |
| 4,848,138 A | | 7/1989 | Marshall |
| 4,865,587 A | | 9/1989 | Walling ........................ 604/97 |
| 4,878,903 A | * | 11/1989 | Mueller ...................... 206/364 |
| 4,944,726 A | * | 7/1990 | Hilal et al. .................. 222/389 |
| 4,968,302 A | | 11/1990 | Schluter et al. |
| 5,168,757 A | * | 12/1992 | Rabenau et al. ....... 604/100.02 |
| 5,224,933 A | | 7/1993 | Bromander .................. 604/99 |
| 5,318,522 A | | 6/1994 | D'Antonio |
| 5,855,546 A | | 1/1999 | Hastings et al. ............... 600/3 |
| 6,090,035 A | | 7/2000 | Campbell et al. |
| 6,099,455 A | | 8/2000 | Columbo et al. |
| 6,102,931 A | | 8/2000 | Thornton .................... 606/194 |

(List continued on next page.)

FOREIGN PATENT DOCUMENTS

| | | |
|---|---|---|
| DE | 44 23 261 A1 | 1/1996 |
| DE | 197 24 223 C1 | 12/1998 |
| EP | 0 351 758 | 1/1990 |
| JP | 2000024001 | 1/2000 |
| WO | WO 98/45191 | 10/1998 |
| WO | WO 00/32271 | 6/2000 |
| WO | WO 00/45627 | 8/2000 |
| WO | WO 00/56249 | 9/2000 |
| WO | WO 00/69503 | 11/2000 |
| WO | WO 00/74778 | 12/2000 |
| WO | WO 00/76557 | 12/2000 |
| WO | WO 01/14011 A1 | 3/2001 |
| WO | WO 01/14617 A1 | 3/2001 |
| WO | WO 01/21106 A1 | 3/2001 |
| WO | WO 01/21245 A1 | 3/2001 |
| WO | WO 01/21248 A1 | 3/2001 |
| WO | WO 01/26734 A1 | 4/2001 |
| WO | WO 01/54764 A2 | 8/2001 |
| WO | WO 01/60443 A1 | 8/2001 |
| WO | WO 01/62331 A1 | 8/2001 |
| WO | WO 01/64123 A1 | 9/2001 |
| WO | WO 01/66188 A1 | 9/2001 |
| WO | WO 01/85255 A1 | 11/2001 |
| WO | WO 01/87400 A1 | 11/2001 |

*Primary Examiner*—William E. Tapolcai
(74) *Attorney, Agent, or Firm*—Crompton Seager Tufte LLC

(57) ABSTRACT

An inflation device such as a syringe is preloaded with gas (other than air) for inflation of balloon catheters. The syringe is lined with, or is packaged within, a low gas-permeability membrane to keep the stored gas from becoming contaminated with air. The physician using the syringe is able to determine whether air has infiltrated the syringe and contaminated the gas stored in the syringe.

14 Claims, 2 Drawing Sheets

U.S. PATENT DOCUMENTS

| | | |
|---|---|---|
| 6,106,454 A | 8/2000 | Berg et al. |
| 6,110,097 A | 8/2000 | Hastings et al. |
| 6,117,065 A | 9/2000 | Hastings et al. |
| 6,142,926 A | 11/2000 | Schneiderman |
| 6,149,574 A | 11/2000 | Trauthen et al. |
| 6,149,575 A | 11/2000 | Leonhardt |
| 6,152,869 A | 11/2000 | Park et al. |
| 6,162,165 A | 12/2000 | Apple et al. |
| 6,179,768 B1 | 1/2001 | Loffler et al. |
| 6,200,256 B1 | 3/2001 | Weinberger |
| 6,200,257 B1 | 3/2001 | Winkler |
| 6,200,307 B1 | 3/2001 | Kasinkas et al. |
| 6,203,485 B1 | 3/2001 | Urick |
| 6,213,976 B1 | 4/2001 | Trerotola |
| 6,217,503 B1 | 4/2001 | Weinberger et al. |
| 6,224,535 B1 | 5/2001 | Chiu et al. |
| 6,224,536 B1 | 5/2001 | Pike |
| 6,231,494 B1 | 5/2001 | Verin et al. |
| 6,231,495 B1 | 5/2001 | Denk |
| 6,231,719 B1 | 5/2001 | Garvey et al. |
| 6,234,951 B1 | 5/2001 | Hastings |
| 6,234,952 B1 | 5/2001 | Lipric |
| 6,238,332 B1 | 5/2001 | Kanesaka |
| 6,241,719 B1 | 6/2001 | Wallace et al. |
| 6,248,057 B1 | 6/2001 | Mavity et al. |
| 6,251,059 B1 | 6/2001 | Apple et al. |
| 6,254,552 B1 | 7/2001 | Lewis et al. |
| 6,258,019 B1 | 7/2001 | Verin et al. |
| 6,261,219 B1 | 7/2001 | Meloul et al. |
| 6,264,579 B1 | 7/2001 | Odai et al. |
| 6,264,595 B1 | 7/2001 | Delfino et al. |
| 6,264,596 B1 | 7/2001 | Weadock |
| 6,264,598 B1 | 7/2001 | Armini |
| 6,267,717 B1 | 7/2001 | Stoll et al. |
| 6,267,775 B1 | 7/2001 | Clerc et al. |
| 6,283,910 B1 | 9/2001 | Bradshaw et al. |
| 6,283,911 B1 | 9/2001 | Keren |
| 6,287,249 B1 | 9/2001 | Tam et al. |
| 6,296,603 B1 | 10/2001 | Turnlund et al. |
| 6,302,839 B1 | 10/2001 | Chernomorsky et al. |
| 6,306,073 B1 | 10/2001 | Weinberger |
| 6,306,074 B1 | 10/2001 | Waksman et al. |
| 6,309,339 B1 | 10/2001 | Ciezki et al. |
| 6,293,899 B1 | 11/2001 | Sioshansi et al. |
| 6,312,374 B1 | 11/2001 | von Hoffmann |
| 6,319,190 B1 | 11/2001 | Schmidt et al. |
| 6,322,490 B1 | 11/2001 | Stack et al. |

\* cited by examiner

PRELOADED GAS INFLATION DEVICE FOR BALLOON CATHETER

FIELD OF THE INVENTION

The present invention generally relates to closed volume inflation devices. In particular, the present invention relates to inflation devices such as syringes used to inflate and deflate balloon catheters.

BACKGROUND OF THE INVENTION

Balloon catheters are sometimes inflated with gas, rather than liquid, because the balloon can be inflated and deflated more quickly than a comparable volume of saline or other liquid inflation media. Gas inflation has proved particularly useful in inflation of balloon centering catheters used in radiation therapy, which relies on a centering balloon to prevent the radiation source from being too close to one side of the target vessel. The use of gas rather than liquid decreases the amount of attenuation of radiation between the radiation source and the vessel wall.

While gas filled balloons are advantageous in some situations, the prior art process of preparing an inflation device for gas inflation is much more complicated than that for liquid inflation. Although air would be relatively easy to load into an inflation device, air is not a suitable inflation medium, because air does not rapidly dissolve in blood. In the event that the balloon bursts or leaks, bubbles could be formed in the arterial blood, impeding blood flow. In addition, a chief component of air, nitrogen, is not desirable for balloon inflation because nitrogen gas has thrombogenic properties which may present clinical risks in the event that the balloon bursts. Accordingly, it is desirable to use a gas other than air and to prevent air contamination of the gas used. A preferable gas used for balloon inflation is carbon dioxide.

Many medical facilities have built-in plumbing systems that provide gases such as carbon dioxide. Alternatively, a pressurized gas canister of carbon dioxide may be used. In either case, the pressurized source of carbon dioxide must be connected to a reduction valve to fill the inflation device with gas. The reduction valve lowers the pressure of the gas to a pressure suitable for the syringe. The reduction valve may utilize several stopcocks that must be opened for the gas to flow. For example, a first stopcock may be located at the reduction valve, a second stopcock may be located at the catheter connection point, and a third stopcock may be located at the syringe. Such systems are physically cumbersome and unwieldy, and require considerable preparation time by skilled medical personnel. Accordingly, a desirable feature in an inflation device would be an inflation syringe preloaded with a specified gas which the physician could conveniently use without extensive preparation and equipment.

Unfortunately, however, the storage of gas in a syringe mechanism presents several difficulties. Most plastics used in syringe manufacture are gas-permeable, at least to some extent. In addition, most stopcocks and syringe plungers, even when manufactured to precise specifications, are subject to leakage over extended periods of storage. Finally, packaging materials used to maintain sterility are usually gas permeable to facilitate ETO sterilization. These factors contribute to loss of the stored gas and/or contamination of the stored gas by air.

SUMMARY OF THE INVENTION

The preloaded inflation device of the present invention is suitable for inflating and deflating a wide variety of balloon catheters such as a centering balloon catheter or an angioplasty balloon catheter. In addition, although described with specific reference to a syringe type inflation device for purposes of illustration, other closed volume inflation devices are within the scope of the present invention.

The present invention provides several embodiments of an inflation device preloaded with an inflation gas (other than air). As used herein, the term inflation gas refers to any gas, other than air, that is suitable for balloon catheter inflation such as carbon dioxide gas. The present invention also provides means for preventing air contamination of the inflation gas contained in the inflation device. In addition, the present invention enables the user to positively confirm that no air contamination of the inflation gas stored in the inflation device has occurred.

The present invention generally provides for an inflation device which is preloaded with an inflation gas, such as carbon dioxide gas, for balloon inflation. The inflation device is preferably preloaded by the manufacturer and/or packager of the inflation device. The inflation device generally has a body with a chamber preloaded with the inflation gas, and includes some means for preventing air contamination of the inflation gas. The means for preventing air contamination may vary according to the particular embodiment of the invention.

In a first embodiment of the present invention, a syringe is preloaded with a gas suitable for balloon inflation, such as carbon dioxide, and then placed in a container such as a pouch or envelope that has low gas-permeability. The container is filled with the same gas as that loaded into the syringe, at approximately the same pressure, after which the container is sealed. Because the container has low gas-permeability, air is not able to enter the container, or the syringe. Although the gas stored in the syringe may exchange with that in the container, there is no contamination since the gases are similar. After the container is sealed, the entire syringe and package may be sterilized with a non-gas based sterilization process, such as gamma or e-beam radiation, in accordance with existing techniques.

In another embodiment of the present invention, the syringe may contain within its main body a capsule of gas, the capsule being made of a gas-impermeable membrane. When the syringe is ready for use, the capsule may be broken or otherwise opened by piercing or cutting the membrane. For example, the capsule may be broken manually with a sterile pin. Alternatively, the syringe may contain a small pin or other sharp object pointing generally towards the proximal end of the syringe which punctures the gas capsule when the gas capsule is pressed forward by compression of the syringe plunger. In a preferred embodiment, the capsule is formed in a manner which does not interfere with the compression of the syringe plunger (i.e., the plunger will not get entrapped on the compressed capsule).

In a further embodiment of the present invention, the inflation gas is stored in a syringe that is sealed by a membrane, preferably located at the distal opening of the syringe. Although the gas contained within the syringe may pass in minute quantities through the plunger seal, the distal sealing membrane, or the syringe body itself, particularly if the syringe tubular body is constructed of a plastic material which is gas-permeable, air contamination is detectable by having a-nitrogen-sensing strip packaged within the syringe. When the syringe is to be used, the membrane at the distal opening of the catheter may be cut, punctured, or otherwise opened. With this embodiment, a small strip is treated or coated with a chemical that changes appearance (e.g., color)

in the presence of an unacceptable amount of nitrogen gas. A nitrogen sensing strip may also be disposed in the pouch containing the syringe in the first embodiment. At the time of use, the color of the strip may be checked to ensure that an unacceptable amount of air has not infiltrated the syringe.

DETAILED DESCRIPTION OF THE PRESENT INVENTION

The following detailed description should be read with reference to the drawings in which similar elements in different drawings are numbered the same. The drawings, which are not necessarily to scale, depict illustrative embodiments and are not intended to limit the scope of the invention.

As mentioned previously, each preloaded inflation device embodiment of the present invention is suitable for inflating and deflating a wide variety of balloon catheters such as centering balloon catheters and angioplasty balloon catheters. In the field of intravascular ionizing radiation therapy, gas inflation of centering balloon catheters is particularly useful because gas inflation media, as compared to liquid inflation media, decreases the amount of attenuation of radiation between the radiation source and the vessel wall. Accordingly, a system comprising an inflation device as described herein in combination with a balloon catheter, such as a centering balloon catheter or an angioplasty balloon catheter, is within the scope of the present invention. An example of a suitable centering balloon catheter for use in intravascular ionizing radiation therapy is described in European Patent No. 688 580 to Verin et al., which is hereby incorporated in its entirety by reference.

Also as mentioned previously, although described with specific reference to a syringe type inflation device for purposes of illustration, other closed volume inflation devices are within the scope of the present invention. For example, all types of piston and barrel inflation devices are contemplated by the present invention.

The present invention provides several embodiments of an inflation device preloaded with an inflation gas (other than air). As used herein, the term inflation gas refers to any gas, other than air, that is suitable for balloon catheter inflation. Carbon dioxide gas is the preferred choice, but other non-thrombogenic gases or mixtures with high solubility in blood may be employed.

Figure 1:
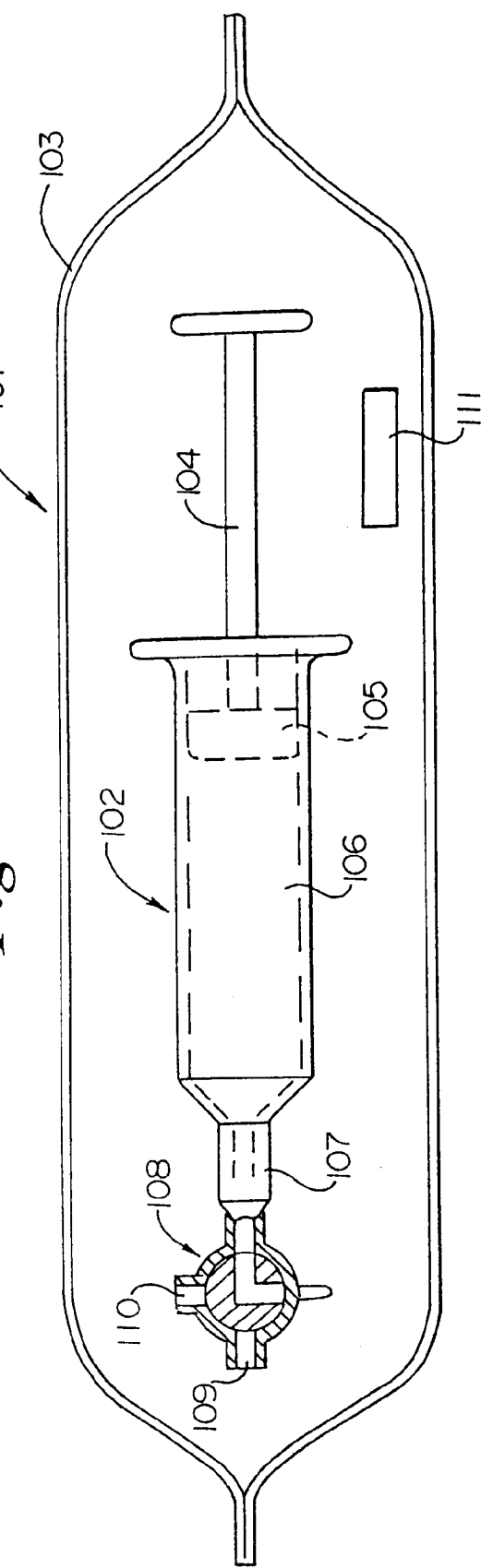
FIG. 1 is a plan view of an inflation device and package in accordance with a first embodiment of the present invention, showing a syringe preloaded with an inflation gas and packaged in a gas-impermeable pouch.

With reference to FIG. 1, a first embodiment of the present invention utilizes a pouch 103 having low gas permeability to prevent air from infiltrating the inflation device 102. The end-user (physician, clinician, or lab tech) receives the packaged inflation device shown generally at 101, including a syringe 102 disposed in the low gas permeability pouch 103. The low gas-permeability pouch may be formed of a wide variety of low gas-permeability materials and composites such as metal foils, metal foil/polymer composites, polyethylene terephthalate (PET), PET/aluminum or polyvinyl fluoride (PVF). Instead of a pouch, a hermetically sealed metal container (such as the can in which tennis balls are sold) could be used. At the manufacturing/packaging stage, the syringe 102 may be filled with the inflation gas after which the stopcock 108 is closed. Similarly, the pouch 103 may be filled with the inflation gas after which the pouch is sealed. Conventional techniques may be used to seal the inflation device 102 in the pouch 103, which remains sealed until it is opened by the physician at the time the inflation device 102 is to be used.

The syringe 102, consisting of plunger 104, plunger seal 105, tubular body 106, and reduction tube 107, may be coupled to a balloon catheter (not shown) by a standard stopcock 108 utilizing standard catheter fittings. Because the pouch 103 is formed of low gas-permeability material and since the pouch 103 is filled with the same gas as contained in the syringe 102, the components of the syringe 102 may formed of conventional materials using conventional techniques. However, to further reduce the tendency of the inflation gas to become contaminated with air or other undesirable gases, the components 104, 105, 106 and 107 of the syringe 102, including the stopcock 108, may be formed in part or in whole of materials having low gas-permeability.

The stopcock 108 may be connected to a catheter at port 109, and may be further coupled to an evacuation or aspiration syringe at port 110. Alternately, the reduction tube 107 may utilize a standard catheter fitting and be connected directly to the desired catheter. Those skilled in the art will recognize that many suitable means may be used to connect the inflation device 102 to any desired catheter without departing from the present invention.

Preferably, the volume of inflation gas within the syringe 102 is equal to or greater than the volume required to inflate the desired balloon catheter. For example, for PTCA (percutaneous translumenal coronary angioplasty) balloon catheters and other coronary balloon catheters (e.g., centering catheters), as much as 3cc to 20cc is required due to the high compressability of gas. Note that the inflation gas volume may be adjusted for differences in pressure and temperature between the manufacturing/packaging stage and the end use stage. The syringe 102 may have graduated indications of volume that can be referred to by a physician to determine an approximate volume of inflation gas contained in the syringe 102.

The embodiment illustrated in FIG. 1 may further include a nitrogen-sensing indicator strip 111 located inside the pouch 103 as shown and/or in the body 106 of the syringe 102. The nitrogen-sensing indicator strip 111 visually indicates (e.g., by color change) the presence of nitrogen gas. The nitrogen-sensing indicator strip 111 comprises a small strip of substrate which is treated or coated with a chemical reagent that changes appearance (e.g., color) in the presence of nitrogen gas. Alternatively, a small strip of calcium metal, for example, that changes appearance in the presence of nitrogen may be used, as detailed in U.S. Pat. No. 4,848,138 to Marshall, which is hereby incorporated by reference in its entirety.

If the nitrogen indicator strip 111 is located inside the pouch 103, it may be viewed through transparent pouch 103 prior to opening. If the nitrogen indicator strip 111 is located inside the syringe body 106, it may be viewed through transparent or translucent syringe tubular body 106. Thus, the nitrogen-sensing indicator strip 111 indicates whether the inside of the pouch 103 and/or the inside of the syringe has been infiltrated by air during shipment or storage. In this manner, the nitrogen-sensing strip 111 may be used to ensure and confirm that the inflation gas has not been contaminated.

Figure 2:
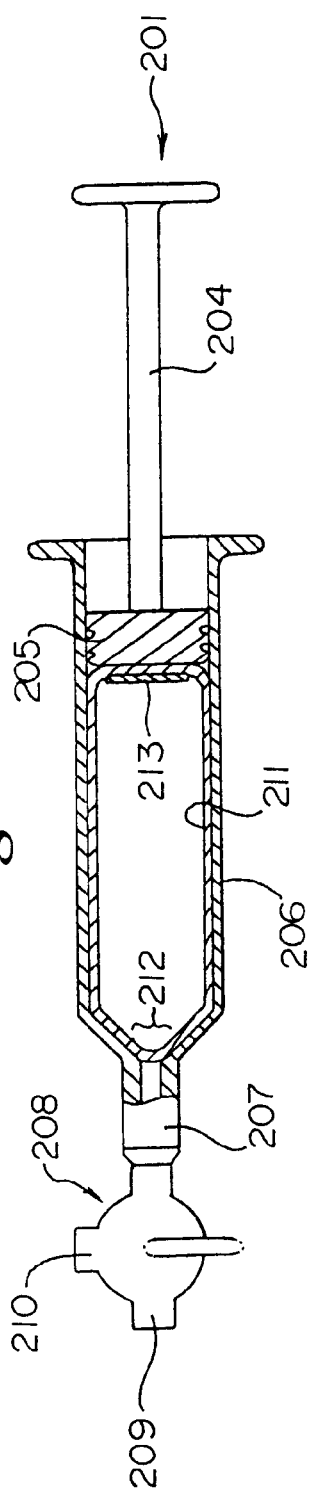
FIG. 2 is a cross-sectional view of an inflation device (package not shown) in accordance with an alternative embodiment of the present invention, showing a syringe containing a gas-impermeable capsule preloaded with an inflation gas.

With reference to FIG. 2, a cross-sectional view of an inflation device 201 (package not shown) in accordance with an alternative embodiment of the present invention is shown. Except as described herein, the inflation device 201 illustrated in FIG. 2 is the same as inflation device 102 described with reference to FIG. 1. The inflation device illustrated in FIG. 2 is shown as a syringe 201 which includes a plunger 204, a plunger seal 205, a tubular body 206, and a reduction tube 207 which is connected to a standard stopcock 208 with catheter connection 209 and evacuation syringe connection 210. The syringe 202 further contains within the tubular body 206 a sealed gas capsule 211, which is constructed from a low gas-permeability membrane. Suitable materials for the low gas permeability membrane forming the capsule 211 include the materials described previously with reference to pouch 103. The capsule 211 is filled during the manufacturing/packaging stage with the inflation gas, and may be placed in the body 206 of the syringe 201 at the same stage or just prior to use.

Although a low gas-permeability pouch 103 filled with an inflation gas as described with reference to FIG. 1 is not necessary for packaging inflation device 201, such a pouch 103 may be used with this embodiment to further ensure that no contamination of the inflation gas stored in the capsule 211 takes place. In addition, a nitrogen sensing strip 213 similar to strip 111 may be placed in the capsule 211 in order to confirm that the inflation gas stored in the capsule 211 has not been contaminated by air.

Prior to use, the low gas-permeability membrane forming the capsule 211 may be punctured or otherwise opened with a sterile needle inserted through the reduction tube 207 (with the stopcock 208 temporarily taken off). Preferably, in order to facilitate easy puncturing, the capsule 211 is sufficiently filled with inflation gas such that the membrane expands to contact the inner wall of the body 206 and plunger seal 205. Alternatively, rather than using a puncturing mechanism, the capsule 211 may have a thinner walled membrane 212 at the part of the capsule 211 adjacent the reduction tube 207 of the syringe 201. In this manner, when the syringe plunger 204 is depressed, the capsule 211 will break in the area 212 under the increased pressure inside the capsule.

Puncturing the membrane of the capsule 211 may be done after confirming that no air has infiltrated the capsule 211 by checking the nitrogen indicator strip 213 through the transparent or translucent wall of tubular body 206.

Figure 3:
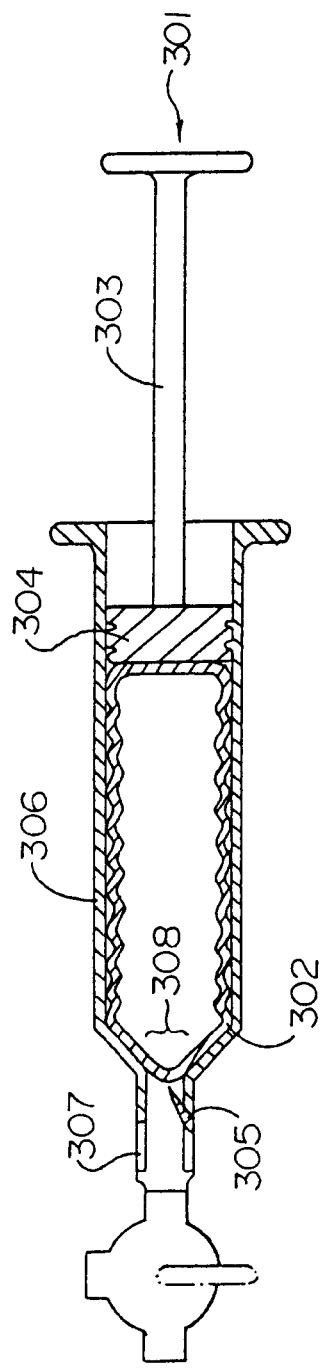
FIG. 3 is a cross-sectional view of an alternate embodiment of the inflation device illustrated in FIG. 2, wherein the capsule is articulated and further including a puncturing device for puncturing the capsule.

Aside from the thin-walled area 212, the membrane forming the capsule 211 may have a relatively uniform profile and wall thickness. Alternatively, an articulated capsule 302 may be used as illustrated in FIG. 3. Except as described herein, the inflation device 301 illustrated in FIG. 3 is the same as inflation device 201 described with reference to FIG. 2. The membrane forming the articulated capsule 302 includes a plurality of small reversing folds resembling those of a bellows or accordion. As the plunger 303 is compressed to expel inflation gas from the capsule 302, the collapsing capsule 302 does not interfere with the movement of the plunger 303 in the tubular body 306. In other words, the plunger 303 and the plunger seal 304 will not catch or jam on the capsule membrane 302 as it is compressed.

Also shown in FIG. 3, the present invention may have a self-puncturing means 305, fitted within or otherwise attached to the inside of reduction tube 307. Of course, the self-puncturing means 305 may also be used with syringe 201 to puncture the membrane of capsule 211. In addition, those skilled in the art will recognize that many suitable alternative puncturing mechanisms may be employed in addition to the mechanisms disclosed herein. The self-puncturing means 305 perforates or punctures the membrane of the capsule 302 when pressure is exerted on the capsule 302 by plunger 303. The pressure of the inflation gas in the capsule 302 will provide greater resistance to the syringe plunger 303 initially, until the capsule 302 is forced at its distal end 308 into the puncturing pin 305. The self-puncturing means 305 increases the convenience of the syringe, because no additional puncturing actions are required other than merely depressing the syringe plunger 303.

As shown in FIG. 3, the puncturing pin may be embedded in the syringe reduction tube 307 wall. Alternatively, the puncturing pin 305 may simply be adhesively connected to the inside of the reduction tube 307. Embedding the pin 305 may be accomplished by insert molding the pin 305 in the wall of the reduction tube 307. Alternately, the pin 305 may be forced through the wall of the reduction tube 307, with or without a pilot hole, and with or without the use of adhesive, to extend through the wall and into the lumen of the reduction tube 307.

Figures 4A, 4B:
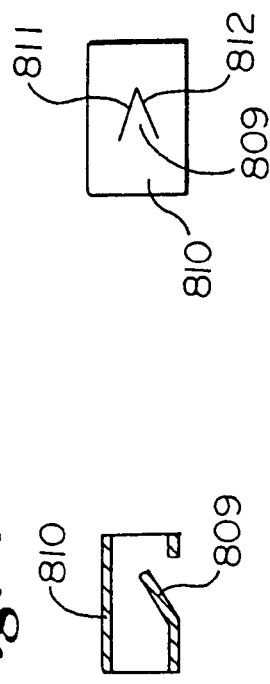
FIGS. 4A and 4B are cross-sectional and plan views respectively of an alternative puncturing device for use with embodiments of FIGS. 2 and 3.

An alternative puncturing member 813 is illustrated in FIGS. 4A and 4B. The self-puncturing member 809 may be used with syringe 201 to puncture the membrane of capsule 211 or with syringe 301 to puncture the membrane of capsule 302. The puncturing member 809 is formed from a tubular metallic member 810. Puncturing member 809 is formed in tubular metallic member 810 by making two cuts 811 and 812 that meet at the point of puncturing member 809. Puncturing member 809 is then bent inward toward the middle of tubular metallic member 810. As depicted in FIG. 8A, after being bent in, the puncturing member 813 intrudes into the lumen of the tubular metallic member. This tubular metallic member 810 may be press fit into the syringe reduction tube 207 or 307. When placed in the reduction tube 207 or 307, the puncturing member 809 is in a position to puncture the gas-impermeable capsule 211 or 302 when the membrane intrudes into the lumen of tubular metallic member 810. Furthermore, it is contemplated that puncturing may take place automatically during the process of attaching the catheter to the syringe.

From the foregoing, it should be apparent to those skilled in the art that the present invention generally provides for various embodiments of inflation devices 102, 201, 301, 402 which are preloaded with an inflation gas, such as carbon dioxide gas, for balloon inflation. The inflation devices are preferably preloaded by the manufacturer and/or packager. Each inflation device generally has a body with a chamber preloaded with the inflation gas, and each device includes some means for preventing air contamination of the inflation gas. The means for preventing air contamination may vary according to the particular embodiment as described above.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An inflation device, comprising:

a body having a chamber therein;

an inflation gas other than air contained in the chamber; and means for preventing air contamination of the inflation gas.

2. An inflation device as in claim 1, wherein the inflation gas comprises carbon dioxide.

3. An inflation device as in claim 1, wherein the body comprises a syringe.

4. An inflation device as in claim 1, further comprising a nitrogen detection strip disposed in the chamber.

5. An inflation device as in claim 1, wherein the contamination preventing means comprises a gas-impermeable sealed container enclosing the body and containing a gas other than air.

6. An inflation device as in claim 5, wherein the gas in the container comprises the inflation gas.

7. An inflation device as in claim 1, wherein the contamination preventing means comprises a gas-impermeable sealed capsule disposed in the chamber and containing the inflation gas.

8. An inflation device as in claim 7, wherein the sealed capsule is articulated.

9. An inflation device as in claim 7, further comprising a puncturing member disposed adjacent the capsule such that the capsule is punctured by the puncturing member upon compression of the capsule.

10. An inflation device as in claim 9, wherein the puncturing member comprises a tubular member having a sharp protrusion.

11. A method of filling a chamber in an inflation device with a gas, comprising the steps of:

filling the inflation device chamber with an inflation gas other than air at a pressure greater than one atmosphere; and sealing the distal opening of the inflation device with a puncturable membrane which prevents the inflation gas from escaping.

12. A packaged inflation device for inflating a balloon catheter, comprising:

a pressure source comprising:

a chamber;

a plunger disposed in the chamber;

an inflation gas other than air stored in said chamber; and a gas-sealed container, wherein the pressure source is disposed within said container, the container being filled with the same gas as the chamber.

13. An inflation device for inflating a balloon catheter, comprising:

a chamber;

a low gas-permeability membrane disposed in the chamber and being formed into a hollow capsule, the capsule containing an inflation gas, the membrane being sealed so as to isolate the inflation gas from the atmospheric gases outside the capsule.

14. A syringe for holding and delivering gas inflation media for inflation of balloon catheters, comprising:

a tubular body member having an inner lumen, a tube wall, and distal and proximal ends, said tubular body being filled with a gas at a pressure greater than one atmosphere;

a reduction tube having an inner lumen, a tube wall, and distal and proximal ends, joined to the distal end of the tubular body member, the reduction tube inner lumen being narrower than the tubular body inner lumen, and being in fluid communication with the tubular body member;

a fitting disposed at the distal end of the reduction tube;

a plunger member disposed within the tubular body; and a distal membrane disposed at the distal end of the chamber, the distal membrane isolating the inflation gas from atmospheric gases outside the syringe.

* * * * *

UNITED STATES PATENT AND TRADEMARK OFFICE
CERTIFICATE OF CORRECTION

PATENT NO.      : 6,471,671 B1
DATED           : October 29, 2002
INVENTOR(S)     : M.J. Urick et al.

It is certified that error appears in the above-identified patent and that said Letters Patent is hereby corrected as shown below:

<u>Title page,</u>
Item [56], References Cited, FOREIGN PATENTS, insert -- WO 01/47602 A1 7/2001 --
U.S. PATENT DOCUMENTS, insert -- 6,146,322  11/2000  Papirov et al. --

Signed and Sealed this

Sixteenth Day of September, 2003

JAMES E. ROGAN
*Director of the United States Patent and Trademark Office*